US008088058B2

(12) United States Patent
Juliana et al.

(10) Patent No.: US 8,088,058 B2
(45) Date of Patent: Jan. 3, 2012

(54) ARTICULATING ARM

(75) Inventors: Vincent A. Juliana, Chester Springs, PA (US); Mark Edward Riehl, Doylestown, PA (US); Ravi Pillutla, Audubon, PA (US)

(73) Assignee: Neuronetics, Inc., Malvern, PA (US)

( * ) Notice: Subject to any disclaimer, the term of this patent is extended or adjusted under 35 U.S.C. 154(b) by 1456 days.

(21) Appl. No.: 11/039,267

(22) Filed: Jan. 20, 2005

(65) Prior Publication Data

US 2006/0161039 A1    Jul. 20, 2006

(51) Int. Cl.
*A61N 1/00* (2006.01)
(52) U.S. Cl. ............................................... 600/15; 600/9
(58) Field of Classification Search ............... 600/9–15; 248/121–124.1; 606/130; 128/897
See application file for complete search history.

(56) References Cited

U.S. PATENT DOCUMENTS

| | | | | |
|---|---|---|---|---|
| 2,613,725 A | * | 10/1952 | Woodhall | 297/363 |
| 3,683,923 A | | 8/1972 | Anderson | 128/303.14 |
| 3,818,516 A | * | 6/1974 | Hopper et al. | 5/611 |
| 4,473,074 A | | 9/1984 | Vassiliadis | 128/303.1 |
| 4,638,798 A | | 1/1987 | Shelden et al. | 128/303 |
| 4,712,558 A | | 12/1987 | Kidd et al. | |
| 4,995,395 A | | 2/1991 | Ilmoniemi et al. | |
| 5,097,833 A | | 3/1992 | Campos | 128/421 |
| 5,116,304 A | | 5/1992 | Cadwell | |
| 5,254,123 A | | 10/1993 | Bushey | 606/130 |
| 5,299,569 A | | 4/1994 | Wernicke et al. | 607/45 |
| 5,370,117 A | | 12/1994 | McLaurin, Jr. | |
| 5,609,565 A | * | 3/1997 | Nakamura | 600/229 |
| 5,655,534 A | | 8/1997 | Ilmoniemi | 128/653.1 |
| 5,707,334 A | | 1/1998 | Young | |
| 5,725,471 A | | 3/1998 | Davey et al. | 600/13 |
| 5,749,362 A | | 5/1998 | Funda et al. | |
| 5,769,778 A | | 6/1998 | Abrams et al. | |
| 5,812,301 A | | 9/1998 | Nakamura et al. | 359/384 |
| 5,813,970 A | | 9/1998 | Abrams et al. | |

(Continued)

FOREIGN PATENT DOCUMENTS

DE    10242542 A1    4/2004

(Continued)

OTHER PUBLICATIONS

Awiszus, F. et al., "Characterization of Paired-Pulse Transcranial Magnetic Stimulation Conditions Yielding Intracortical Inhibition of I-Wave Facilitation using a Threshold Paradigm", *Experimental Brain Research*, 1999, 129, 317-324.

(Continued)

*Primary Examiner* — Charles A Marmor, II
*Assistant Examiner* — Carrie Dorna
(74) *Attorney, Agent, or Firm* — Condo Roccia LLP

(57) ABSTRACT

Just one embodiment of the invention includes a device, method and system for positioning a treatment instrument with respect to a patient. The novel device includes a holder for securing the treatment instrument (e.g., a magnetic stimulation device used for transcutaneous magnetic stimulation treatment of depression). The holder allows the treatment instrument to move about the patient. The device also includes a first arm that is coupled to the holder, and a vertical support that is coupled to the first arm. The first arm is substantially transverse to the vertical support, and may rotates about the vertical support in a horizontal axis. Such rotation, as well as movement and rotation of other components with respect to each other may be facilitated by a ball bearing construction.

65 Claims, 5 Drawing Sheets

U.S. PATENT DOCUMENTS

| | | | |
|---|---|---|---|
| 5,820,623 A | 10/1998 | Ng | 606/1 |
| 5,828,770 A | 10/1998 | Leis et al. | 382/103 |
| 5,855,582 A | 1/1999 | Gildenberg | |
| 5,923,417 A | 7/1999 | Leis | 356/141.1 |
| 6,061,644 A | 5/2000 | Leis | 702/153 |
| 6,066,084 A | 5/2000 | Edrich et al. | |
| 6,080,164 A * | 6/2000 | Oshio et al. | 606/130 |
| 6,086,525 A | 7/2000 | Davey et al. | 600/13 |
| 6,099,459 A * | 8/2000 | Jacobson | 600/13 |
| 6,117,066 A | 9/2000 | Abrams et al. | |
| 6,122,541 A * | 9/2000 | Cosman et al. | 600/426 |
| 6,169,963 B1 | 1/2001 | Markov | |
| 6,179,771 B1 | 1/2001 | Mueller | 600/13 |
| 6,198,958 B1 | 3/2001 | Ives et al. | |
| 6,210,317 B1 | 4/2001 | Bonlie et al. | 600/9 |
| 6,253,109 B1 | 6/2001 | Gielen | |
| 6,256,531 B1 | 7/2001 | Ilmoniemi et al. | 600/544 |
| 6,279,579 B1 | 8/2001 | Riaziat et al. | 128/897 |
| 6,288,785 B1 | 9/2001 | Frantz et al. | 356/614 |
| 6,366,814 B1 | 4/2002 | Boveja et al. | |
| 6,389,318 B1 | 5/2002 | Zarinetchi et al. | 607/61 |
| 6,402,678 B1 | 6/2002 | Fischell et al. | |
| 6,418,345 B1 | 7/2002 | Tepper et al. | |
| 6,425,852 B1 * | 7/2002 | Epstein et al. | 600/13 |
| 6,463,328 B1 | 10/2002 | John | 607/45 |
| 6,480,743 B1 | 11/2002 | Kirkpatrick et al. | |
| 6,484,059 B2 | 11/2002 | Gielen | 607/45 |
| 6,488,617 B1 | 12/2002 | Katz | |
| 6,497,648 B1 | 12/2002 | Rey | 600/14 |
| 6,503,187 B1 | 1/2003 | Ilmoniemi et al. | |
| 6,516,213 B1 | 2/2003 | Nevo | 600/424 |
| 6,516,288 B2 | 2/2003 | Bagne | 702/179 |
| 6,537,197 B1 | 3/2003 | Ruohonen et al. | 600/13 |
| 6,551,233 B2 | 4/2003 | Perreault et al. | |
| 6,553,326 B1 | 4/2003 | Kirsch et al. | 702/65 |
| 6,560,490 B2 | 5/2003 | Grill et al. | 607/72 |
| 6,567,702 B1 | 5/2003 | Nekhendzy et al. | |
| 6,571,123 B2 | 5/2003 | Ives et al. | 600/544 |
| 6,572,528 B2 | 6/2003 | Rohan et al. | |
| 6,625,563 B2 | 9/2003 | Kirsch et al. | 702/150 |
| 6,827,681 B2 | 12/2004 | Tanner et al. | 600/9 |
| 6,849,040 B2 | 2/2005 | Ruohonen et al. | 600/14 |
| 6,978,179 B1 | 12/2005 | Flagg et al. | 607/45 |
| 2001/0027313 A1 * | 10/2001 | Shimmura et al. | 606/1 |
| 2002/0013612 A1 | 1/2002 | Whitehurst | |
| 2002/0087201 A1 | 7/2002 | Firlik et al. | 607/45 |
| 2002/0091419 A1 | 7/2002 | Firlik et al. | 607/45 |
| 2002/0103515 A1 | 8/2002 | Davey et al. | |
| 2002/0123780 A1 | 9/2002 | Grill et al. | |
| 2002/0160436 A1 | 10/2002 | Markov et al. | |
| 2002/0169355 A1 | 11/2002 | Rohan et al. | |
| 2003/0004392 A1 | 1/2003 | Tanner et al. | 600/9 |
| 2003/0023159 A1 | 1/2003 | Tanner | 600/417 |
| 2003/0028072 A1 | 2/2003 | Fischell et al. | |
| 2003/0050527 A1 | 3/2003 | Fox et al. | 600/13 |
| 2003/0065243 A1 | 4/2003 | Tanner | 600/9 |
| 2003/0073899 A1 | 4/2003 | Ruohonen et al. | 600/417 |
| 2003/0074032 A1 | 4/2003 | Gliner | |
| 2003/0082507 A1 | 5/2003 | Stypulkowski | 434/262 |
| 2003/0088274 A1 | 5/2003 | Gliner et al. | 607/3 |
| 2003/0097161 A1 | 5/2003 | Firlik et al. | 607/72 |
| 2003/0125786 A1 | 7/2003 | Gliner et al. | 607/116 |
| 2003/0130706 A1 | 7/2003 | Sheffield et al. | 607/46 |
| 2004/0010177 A1 | 1/2004 | Rohan et al. | |
| 2004/0019370 A1 | 1/2004 | Gliner et al. | 607/48 |
| 2004/0051279 A1 | 3/2004 | Grant et al. | 280/638 |
| 2004/0077921 A1 | 4/2004 | Becker et al. | |
| 2004/0077923 A1 | 4/2004 | Frimerman et al. | 600/13 |
| 2004/0127942 A1 | 7/2004 | Yomtov et al. | |
| 2004/0138524 A1 | 7/2004 | Ueda et al. | 600/102 |
| 2004/0153129 A1 | 8/2004 | Pless et al. | 607/62 |
| 2004/0172012 A1 | 9/2004 | Otsuka et al. | 606/1 |
| 2004/0193001 A1 | 9/2004 | Miller | 600/9 |
| 2005/0021104 A1 | 1/2005 | DiLorenzo | 607/45 |
| 2005/0049486 A1 * | 3/2005 | Urquhart et al. | 600/429 |
| 2005/0124848 A1 | 6/2005 | Holzner | |
| 2005/0216071 A1 | 9/2005 | Devlin et al. | |
| 2005/0228209 A1 | 10/2005 | Schneider et al. | |
| 2005/0256539 A1 | 11/2005 | George et al. | 607/2 |

FOREIGN PATENT DOCUMENTS

| | | |
|---|---|---|
| EP | 0 998 958 A3 | 5/2000 |
| EP | 1273320 A1 | 1/2003 |
| JP | 1990-071514 A | 3/1990 |
| JP | 2001-516461 A | 9/2001 |
| JP | 2004-215905 A | 8/2004 |
| WO | WO 97/20166 A1 | 6/1997 |
| WO | WO 99/64884 | 12/1999 |
| WO | WO 00/74777 A1 | 12/2000 |
| WO | WO 01/12236 A2 | 2/2001 |
| WO | WO 01/28622 A2 | 4/2001 |
| WO | WO 01/97906 A2 | 12/2001 |
| WO | WO 02/09811 A1 | 2/2002 |
| WO | WO 02/31604 A1 | 4/2002 |
| WO | WO 02/32504 A2 | 4/2002 |
| WO | WO 02/072194 A2 | 9/2002 |
| WO | WO 02/085449 A2 | 10/2002 |
| WO | WO 02/085454 A1 | 10/2002 |
| WO | WO 02/089902 A2 | 11/2002 |
| WO | WO 02/094997 A2 | 11/2002 |
| WO | WO 03/035163 A2 | 5/2003 |
| WO | WO 03/090604 A2 | 11/2003 |
| WO | WO 03/098268 A1 | 11/2003 |
| WO | WO 04/100765 A2 | 11/2004 |
| WO | WO 2005/000401 A1 | 1/2005 |
| WO | WO 2005/065768 A1 | 7/2005 |
| WO | WO 2005/067610 A2 | 7/2005 |
| WO | WO 2006/078727 A2 | 7/2006 |

OTHER PUBLICATIONS

Keiji, I. et al., "Effects of Transcranial Magnetic Stimulation on EEG Activity", *IEEE transactions on Magnetics*, 2002, 38(5), 3347-3349, XP 011075410.

Pascual-Leone, A. et al., "Rapid-Rate Transcranial Magnetic Stimulation of Left Dorsolateral Prefrontal Cortex in Drug-Resistant Depression", *The Lancet*, 1996, 18, 233-237.

Sommer, M. et al., "Increased Transcranial Magnetic Motor Threshold after ECT", *European Archives of Psychiatry and Clinical Neuroscience*, 2002, 252, 250-252.

Baudewig, J. et al., "Functional MRI of Cortical Activations Induced by Transcranial Magnetic Stimulation(TMS)", *Brain Imaging-NeuroReport*, 2001, 12(16), 3543-3548.

Bohning, D.E. Ph.D. et al., "BOLD-fMRI Response to Single-Pulse Transcranial Magnetic Stimulation (TMS)", *Journal of Magnetic Resonance Imaging*, 2000, 11, 569-574.

Bohning, D.E. Ph.D. et al., "A Combined TMS/fMRI Study of Intensity-Dependant TMS over Motor Cortex", *Society of Biological Psychiatry*, 1999, 45, 385-394.

Bohning, D.E. et al., "A TMS Coil Positioning/Holding System for MR Image-Guided TMS Interleaved with fMRI", *Clinical Neurophysiology*, 2003, 114, 2210-2219.

George, M.S. et al., "A Controlled Trial of Daily Left Prefrontal Cortex TMS for Treating Depression", *Society of Biological Psychiatry*, 2000, 48, 962-970.

Grafman, J. Ph.D., "TMS as a Primary Brain Mapping Tool" *Transcranial Magnetic Stimulation in Neuropsychiatry*, 2000, 115-140.

Lisanby, S.H. et al., "Sham TMS: Intracerebral Measurement of the Induced Electrical Field and the Induction of Motor-Evoked Potentials", *Society of Biological Psychiatry*, 2001, 49, 460-463.

Lorberbaum, J.P., M.D. et al., "Safety Concerns of TMS", *Transcranial Magnetic Stimulation in Neuropsychiatry*, 2000, 141-161.

Loo, C.K. et al., "Transcranial Magnetic Stimulation (TMS) in Controlled Treatment Studies: Are Some "Sham" Forms Active?", *Society of Biological Psychiatry*, 2000, 47, 325-331.

Nahas, Z. et al., "Left Prefrontal Transcranial Magnetic Stimulation(TMS) Treatment of Depression in Bipolar Affective Disorder: A Pilot Study of Acute Safety and Efficacy", *Bipolar Disorders*, 2003, 5, 40-47.

Nahas, Z. et al., "Unilateral Left Prefrontal Transcranial Magnetic Stimulation(TMS) Produces Intensity-Dependent Bilateral Effects as Measured by Interleaved BOLD fMRI", *Society of Biological Psychiatry*, 2001, 50, 712-720.

Nahas, Z. et al., "Safety and Feasibility of Repetitive Transcranial Magnetic Stimulation in the Treatment of Anxious Depression in Pregnancy: A Case Report", *J. Clin Psychiatry*, Jan. 1999, 60, 50-52.

Ruohonen, J., "Electroencephalography Combined with TMS", BioMag Laboratory, Helsinki University Central Hospital, http://www.biomag.helsinki.fi/tms/TMSEEG.html, Oct. 6, 1999, 22 pages.

Greene, YM., APA Meeting, Electromagnetic Stimulation Relieves Depression, http://HealthyPlace.com, May 17, 1999, 3 pages.

Pridmore, S., "Substitution of Rapid Transcranial Magnetic Stimulation Treatments for Electroconvulsive Therapy Treatments in a Course of Electroconvulsive Therapy", Depression and Anxiety, 2000, 12, 118-123.

* cited by examiner

ARTICULATING ARM

CROSS-REFERENCE TO RELATED PATENT APPLICATION

The subject matter disclosed herein is related to the subject matter disclosed in the following copending application: U.S. application Ser. No. 10/752,164, which was filed Jan. 6, 2004, and which is incorporated herein by reference.

FIELD OF THE INVENTION

The invention relates to a method and apparatus for positioning a medical device. More specifically, the invention contemplates a positioning system and method for precisely positioning a transcranial magnetic stimulation coil at a treatment location for a patient.

BACKGROUND OF THE INVENTION

Current techniques for positioning medical treatment devices (e.g., magnets for Transcranial Magnetic Stimulation (TMS) studies) typically are simple manual methods or complex robotic approaches designed for research. The manual approaches are very accurate and the complex approaches require expensive and complex imaging or computational systems to determine three dimensional spatial coordinates for positioning reference. Both approaches have severe clinical limitations. The manual methods do not provide a convenient means for repeated and accurate placement, while the three dimensional spatial methods based on imaging modalities are expensive, time consuming, and not conducive to clinical use. A positioning technique for clinical use is desired that provides a simple way for the operator to freely move and place devices, like a TMS magnet, in a time-efficient and inexpensive manner.

In accordance with the conventional manual placement technique, a treatment position on the patient's head or a position used to find a treatment position (i.e., the patient's motor threshold position (MTP)) is determined by a user moving by hand a treatment device near a predicted treatment area. More details of techniques for determining the MTP are also described in related U.S. patent application Ser. No. 10/714,741, filed Nov. 17, 2003, the contents of which are incorporated herein by reference.

The shortcomings of such manual methods is that movement of the device is constrained, making it difficult to determine the proper treatment location. Also, even once the proper location of the treatment area is located, maintaining the device at the proper location is cumbersome. For example, the problem of applying marks to the patient has been addressed in the art by applying a swim cap or similar conformal headgear to the patient and marking the headgear rather than the patient. Of course, this approach requires careful registration of the headgear during subsequent therapy sessions, which is crude, imprecise, and highly operator dependent. Moreover, such an approach still requires accurate coil placement and a mechanism for holding the coil in place.

On the other hand, the Brainsight™ System developed by Rogue Research, Inc. of Montreal, Canada and distributed by Magstim is complex and is designed primarily for research purposes. This system uses diagnostic images from MRI to determine the spatial relationship between internal anatomy and external landmarks and then aligns to the external landmark for therapy or other studies requiring accurate localization. While this approach is useful for research purposes, it is highly impractical and complex and is thus not usable in general clinical practice. Moreover, such techniques have generally been used to overlay coordinate systems onto images and not for identifying particular treatment positions for specific therapies.

Also, other complex methods include the use of robotic, machine-controlled arms for positioning the treatment device with respect to the patient and holding the device in place during treatment. While these techniques provide controlled movement and placement of the coil, they are quite expensive and do not provide for repeatable placement of the coil with respect to a particular patient's head in a clinical setting. As a result, the manual and/or complex imaging techniques described above must also be used for placement of the coil with respect to the patient.

Therefore, there is a need cost-effective and intuitive way of accurately and repeatably positioning a treatment device.

SUMMARY OF THE INVENTION

Just one embodiment of the invention includes a device, method and system for positioning a treatment instrument with respect to a patient. The novel device includes a holder for securing the treatment instrument (e.g., a magnetic stimulation device used for transcutaneous magnetic stimulation treatment of depression). The holder allows the treatment instrument to move about the patient. The device also includes a first arm that is coupled to the holder, and a vertical support that is coupled to the first arm. The first arm is substantially transverse to the vertical support, and may rotates about the vertical support in a horizontal axis. Such rotation, as well as movement and rotation of other components with respect to each other may be facilitated by a ball bearing construction.

In another example embodiment, the first arm has a center of gravity point that is coupled to the vertical support, where the center of gravity point allows the first arm to rotate in a horizontal axis or vertical about the vertical support.

Another example embodiment includes a headrest that may be coupled to a mobile cart and/or the vertical support. The headrest may be adjustable in a vertical and horizontal axis.

Other features of the example embodiment may include a counterbalance coupled to the first arm and affixed to the first arm at a position opposite the holder. The counterbalance operates to hold the treatment instrument in a substantially constant position with respect to the patient. Also, the center may have a curved portion and a center of gravity along one end of the first arm.

The holder also may have a rotating assembly and a downrod that connects the rotating assembly to the first arm. The holder's curved portion may move in an arcuate motion through the rotating assembly. The rotating assembly may be capable of rotating 360 degrees with respect to the first arm, where such rotation is facilitated by a ball bearing construction. Also, the curved portion of the holder may have a radius greater than a patient's head, so as to prevent the curved portion from undesirably contacting the patient's head. Also, the curved portion may be locked as it moves through the rotating assembly.

Another feature of the example embodiment may be a second arm coupled to the vertical support and to the holder, where the second arm maintains the treatment instrument in a substantially constant vertical plane. The example embodiment also may include a locking mechanism that prevents movement of at least one or more of the components of the device. The locking mechanism may be activated by a single activation movement. The single activation movement may include releasing a pushbutton and/or releasing the treatment instrument. The locking mechanism may include electric relays and be activated by a device close proximity to a location that a user grips the treatment instrument.

The treatment instrument may be moved by a first handle and a second handle attached to the treatment instrument. The first handle may extend out from the treatment instrument along an axis defining a center of the treatment instrument and may conform to the shape of a hand. The second handle may extend above the plane of the treatment instrument and may also conform to the shape of a hand.

The example embodiment may include a computing device for processing a position of the treatment instrument with respect to the patient and for storing a position of the treatment instrument with respect to the patient. The computing device may provide the stored position data for subsequent patient treatment. Also, a video display monitor may be included for graphically indicating the position of the treatment instrument with respect to the patient.

An example embodiment of a system for positioning a treatment instrument with respect to a patient also may include a treatment instrument locator device. The treatment instrument locator device may include fiducial reflectors located on the treatment instrument and the patient, and a video camera for determining the position of the treatment instrument and the position of the patient, based on the location of the fiducial reflectors. The video camera may maintain a line of sight to at least one fiducial reflector while the articulating arm is in operation.

Although the invention is discussed in the context of a TMS magnet, it should be appreciated that the treatment instrument may be any treatment instrument. For example, the treatment instrument may be a magnetic stimulation device used for transcutaneous magnetic stimulation treatment of depression. In this embodiment, the magnetic stimulation device may be an arc-shaped core spanning an angle of less than three hundred sixty degrees, where the core comprises a highly saturable magnetic material having a magnetic saturation of at least 0.5 Tesla.

BRIEF DESCRIPTION OF THE DRAWINGS

The above and other features and advantages will become apparent to those skilled in the art based on the following detailed description of the drawing figures, of which.

DETAILED DESCRIPTION OF ILLUSTRATIVE EMBODIMENTS

A detailed description of an illustrative embodiment of the present invention will now be described with reference to FIGS. 1-5. Although this description provides a detailed example of a possible implementation of the present invention, it should be noted that these details are intended to be exemplary and in no way delimit the scope of the invention.

For example, although the invention is discussed in the context of a TMS magnet, it should be appreciated that the treatment instrument may be any treatment instrument. For example, the treatment instrument may be a magnetic stimulation device used for transcutaneous magnetic stimulation treatment of depression. Furthermore, although the device is described with reference the movement of a treatment instrument, it should be appreciated that the device may be used to move and position things other than instruments for the treatment of patients.

Figure 1:
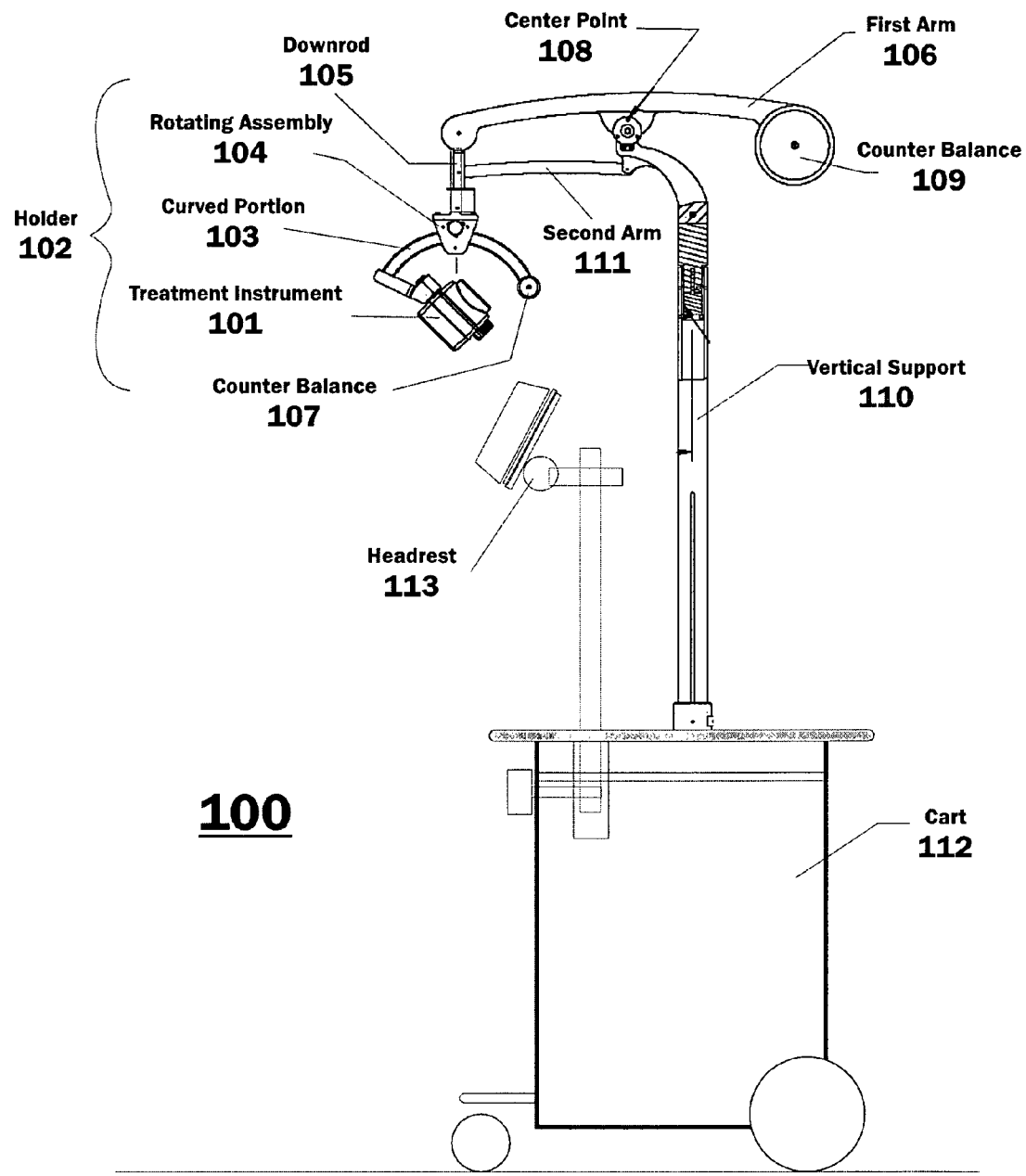
FIG. 1 illustrates a side view of a device for positioning a treatment instrument in accordance with an embodiment of the invention.

FIG. 1 illustrates a side view of a device 100 for positioning a treatment instrument in accordance with an embodiment of the invention. As shown in FIG. 1, device 100 includes a holder 102 for holding a treatment instrument 101. Holder 102 may include all or some of the following components: treatment instrument 101, curved portion 103, rotating assembly 104, and downrod 105.

Treatment instrument 101 may be any type of device used to treat patients. For example, treatment instrument 101 may be a magnetic stimulation device used for transcutaneous magnetic stimulation (TMS) treatment of a patient. Such a magnetic stimulation device may be an arc-shaped core spanning an angle of less than three hundred sixty degrees, where the core comprises a highly saturable magnetic material having a magnetic saturation of at least 0.5 Tesla. Also, although the device is described with reference the movement of an instrument used to treat patients, it should be appreciated that the device may be used to move and position things other than instruments for the treatment of patients.

Treatment instrument 101 is coupled to a curved portion 103 of holder 102. The connection of treatment instrument 101 to curved portion 103 may be accomplished by a coupling that allows treatment instrument 101 to spin or rotate 360 degrees with respect to the curved portion. As will be discussed, the rotation of treatment instrument 101 allows it to be moved freely to any location on the patient.

Curved portion 103 is coupled to a rotating assembly 104, and rotating assembly 104 is coupled to a downrod 105. Downrod 105 is connected to a first arm 106. It should be appreciated that while the components of device 100 are described as being connected to other devices, such connection may allow for rotation about any axis or any connected device, and is not limited to static connection. As a user moves treatment instrument 101 about the patient, curved portion 103 moves through rotating assembly 104 is an arcuate motion. Rotating assembly may include ball bearing or other rotation facilitating components that permit curved portion 103 to move freely through rotating assembly 104. Again, in this way a user is permitted an additional degree of freedom to move treatment instrument 101 about the patient being treated. Also, rotating assembly 104 is able to rotate 360 degrees about downrod 105 and about a first arm 106. Generally, device 100 allows a user to have full flexibility to move treatment instrument 101 about the patient with a full range of motion. There is no restriction in any of the degrees of movement. Therefore, device 100 allows treatment instrument 101 to be moved freely or unencumbered in all axes about the patient.

Curved portion 103 may have a counterbalance 107. Counterbalance 107 may operate to prevent the undesirable movement of curved portion 103 through rotating assembly 104, unless actively moved by a user. Also, curved portion 103 may have a radius greater than a patient's head. By having a greater radius than the patient's head, curved portion 103 may be further prevented from inadvertently from contacting the patient's head. In addition to the use of a counterbalance, as will be discussed, rotating assembly 104 may have a locking mechanism (not shown) that allows the user to lock curved portion 103 into position with respect to rotating assembly 104.

First arm 106 also has a counterbalance 109 and a center point 108. Counterbalance 109 may have a predetermined weight, based on the characteristics of the other components of device 100. Also, center point 108 may have a predetermined location, based on the characteristics of the other components of device 100. Center point 108 permits first arm to rotate in a way that allows holder 102 to move in a vertical direction. Also, center point 108 may permit first arm 106 to rotate 360 degrees about a vertical support 110. As first arm 106 moves holder 102 vertically via center point 108, a second arm 111 may be used to ensure that holder moves substantially in a vertical direction and not also in a horizontal direction (e.g., toward and away from vertical support).

The weight of counterbalance 109, the positioning of center point 108, and the length of first arm 106 all act to maintain the positioning and facilitate the user's movement and positioning of holder 102 and its elements relative to the patient. Although counterbalance 109 is illustrated an end of first arm 106, it should be appreciated that counterbalance 109 may be positioned at any location on first arm 106.

Device 100 also may include a headrest 113. Headrest 113 may serve to support the patient's head, or other body part that is undergoing treatment. Also, although not shown, headrest 113 may be specifically designed to accommodate the features of the head or other anatomy. Headrest 113 may be attached to mobile cart 112, as shown. Also, it should be appreciated that headrest 113 may be freestanding, attached to another component of device 100, and/or may be attached to vertical support. Headrest 113 may be used to stabilize and maintain the positioning of the patient, while the user moves treatment instrument 101 into proper position for treatment. Also, headrest 113 may be made to move in any position with respect to the patient. For example, headrest 113 may be moved in a vertical position with respect to mobile cart 112. Also, headrest 113 may be able to rotate in any direction with respect to the patient's head to accommodate the patient. For example, headrest 113 may angle down or up to accommodate the tilt of the patient's head. Also, headrest 113 may adjust at an angle that allows the patient to move their head in a side-to-side motion. In this way, the user will not be limited to any typical standing or seating arrangement (e.g., chair) to treat the patient.

Headrest 113 may move in a horizontal direction with respect to mobile cart 112. Also, it should be appreciated that although headrest 113 is shown attached to mobile cart 112 and movable in both horizontal and vertical directions, headrest 113 may be attached to mobile cart 112 or attached to another component in a way that facilitates free movement of headrest 113 in any direction with respect to the patient and/or device 100.

Although vertical support 110 is shown attached to first arm 106 at center point 108, it should be appreciated that vertical support may support first arm 106 at any location. Also, vertical support 110 may be made to freely move in any direction with respect to mobile cart 112. For example, vertical support may be made to move freely in a direction toward and away from headrest 113. In this way, if a patient's head has been placed in headrest and is immobilized, the user of device 100 may be permitted to move vertical support 110 is a direction toward headrest 113 and the patient. At the conclusion of the treatment, the user may be able to move vertical support 110 and the rest of the components of device 100 in a direction away from the patient. This movement also allows the patient to safely and comfortably enter and/or move away from device 100 at the beginning or completion of treatment. In addition, first arm 106 may not extend beyond a plane of cart 112 for the safety of the user and the patient.

Although device 100 is shown attached to a cart 112, it should be appreciated that the components of device 100 may be affixed to other devices. For example, device 100 may be placed on a fixed device. Also, device 100 may be attached to a wall, floor, or other structural detail.

Although not shown in FIG. 1, device 100 may include one or more locking mechanisms. The locking mechanisms may prevent movement of at least one or more of the components of device 100. For example, the locking mechanisms may prevent movement of at least one of the following: the treatment instrument, the curved portion, the rotating assembly, the vertical support, and/or the first arm. Such locking may occur by a braking device located within the point of movement or rotation of the component.

Activation of the locking mechanism may occur by a number of techniques. For example, the locking mechanism of all or some of the components may be activated by a single activation movement. The single activation movement may include releasing a pushbutton and/or releasing the treatment instrument. The locking mechanism may include electric relays and be activated by a device close proximity to a location that a user grips the treatment instrument. Also, of course, the activation movement may be activated by more than one activation movement.

Figure 2:
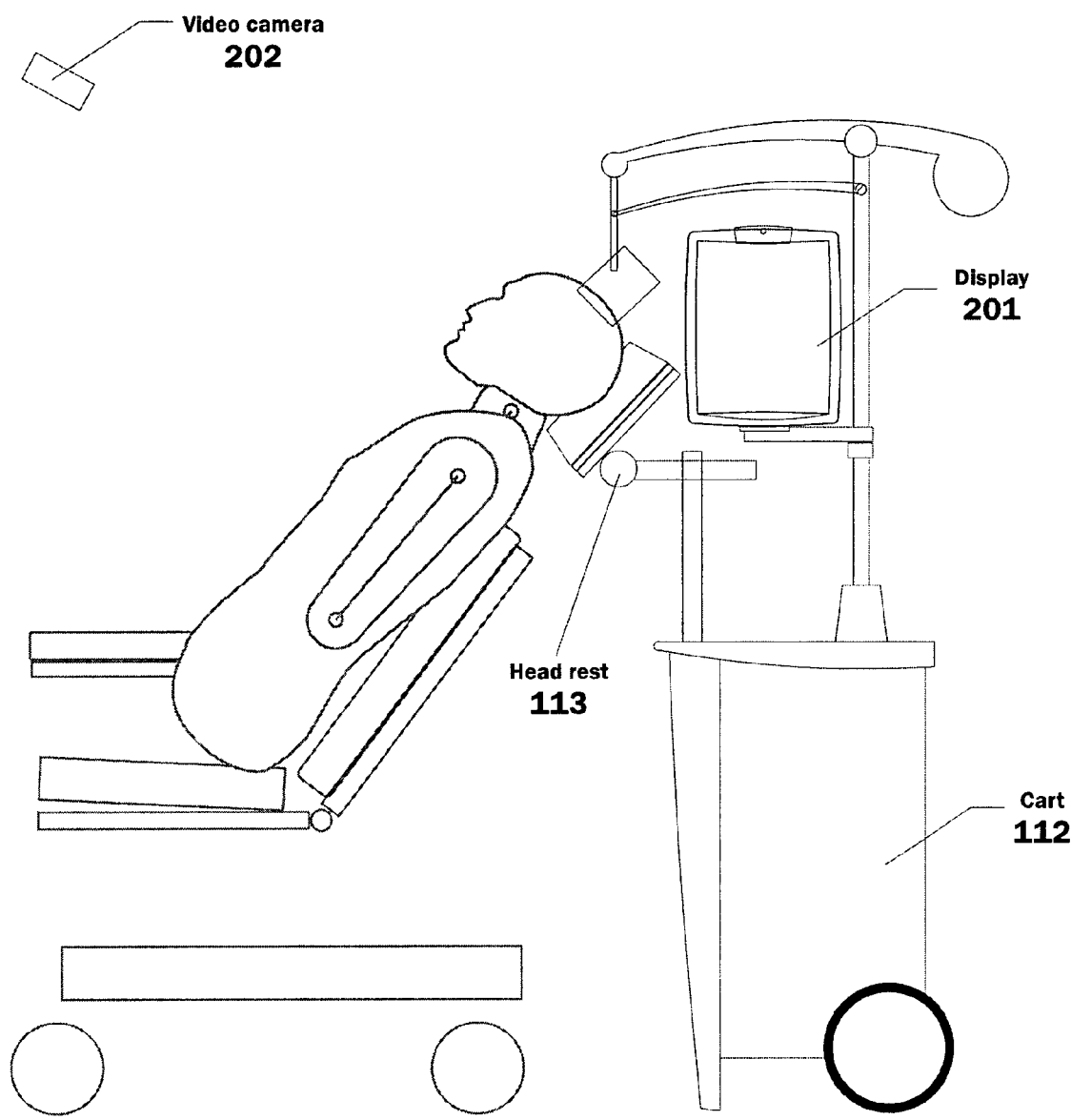
FIG. 2 illustrates another side view of a device for positioning a treatment instrument in accordance with an embodiment of the invention.

FIG. 2 illustrates another side view of device 100 for positioning a treatment instrument in accordance with an embodiment of the invention. As shown in FIG. 2, a display 201 may be located between holder 102 and vertical support 110. Display 201 may be attached to vertical support 110, as shown in FIG. 2. Also, display 201 may be attached separately to cart 112 or attached to another structural device (not shown). There is no limitation in the invention as to how display 201 is configured to operate with device 100.

Display 201 may provide the user with an indication of the positioning of holder 102 and/or treatment instrument 101 with respect to the patient. For example, display 201 may provide a graphical user interface that allows the user to see the position of treatment instrument 101 with respect to the desired treatment position. Also, display 201 may allow the user to graphically see the position and rotation of treatment instrument 101 at any particular moment.

The image may be provided to display 201 via a computing device (not shown) that is capable of processing the images associated with the position of holder 102 and/or treatment instrument 101, as well as the position of the patient. The image presented to the user by the computing device may be any image that enables the user to properly locate the holder 102 and/or treatment instrument 101 with respect to the patient. The image provided by the computing device also may be that of the patient and/or treatment area for the same purpose. Also, the computing device may provide the stored position data for subsequent patient treatment.

The positioning data may be provided to the computing device by any of a number of techniques. For example, the positioning data may be provided by a video camera system 202 that includes a camera and a number of fiducial markers. Video camera 202 may operate to sense the location of the fiducial markers. For example, the fiducial markers may be of a certain material to allow video camera 202 to receive and process their location in space.

The fiducial markers may be placed on any of the components whose location needs to be tracked. For example, fiducial markers may be placed on holder 102 and/or treatment instrument 101. Also, one or more fiducial markers may be placed on the patient's head or other part of the anatomy that is being treated. In this way, as the item with the fiducial markers move (e.g., treatment instrument 101) video camera 202 tracks those movements and provides an indication of those movements to the computing system and the display 201. Also, because the fiducial markers may be placed on more than one item, the video camera may feed signals of the positioning of a particular item with respect to another moving or stationary item.

It should be appreciated that tracking the movement of any component of device 100 is contemplated within the scope of the invention. For example, it may be desirable to track the position of any moving components or stationary components that are attached to other moving items. Also, it should be appreciated that the invention contemplates tracking any part of the patient, including the area to be treated (e.g., head for the treatment of depression using TMS). Furthermore, in addition to tracking for the purposes of facilitating treatment, it may be desirable to track other items for other purposes. For example, it may be desirable to track the location of the user for the purposes of testing and improving the usability of device 100.

Figure 3:
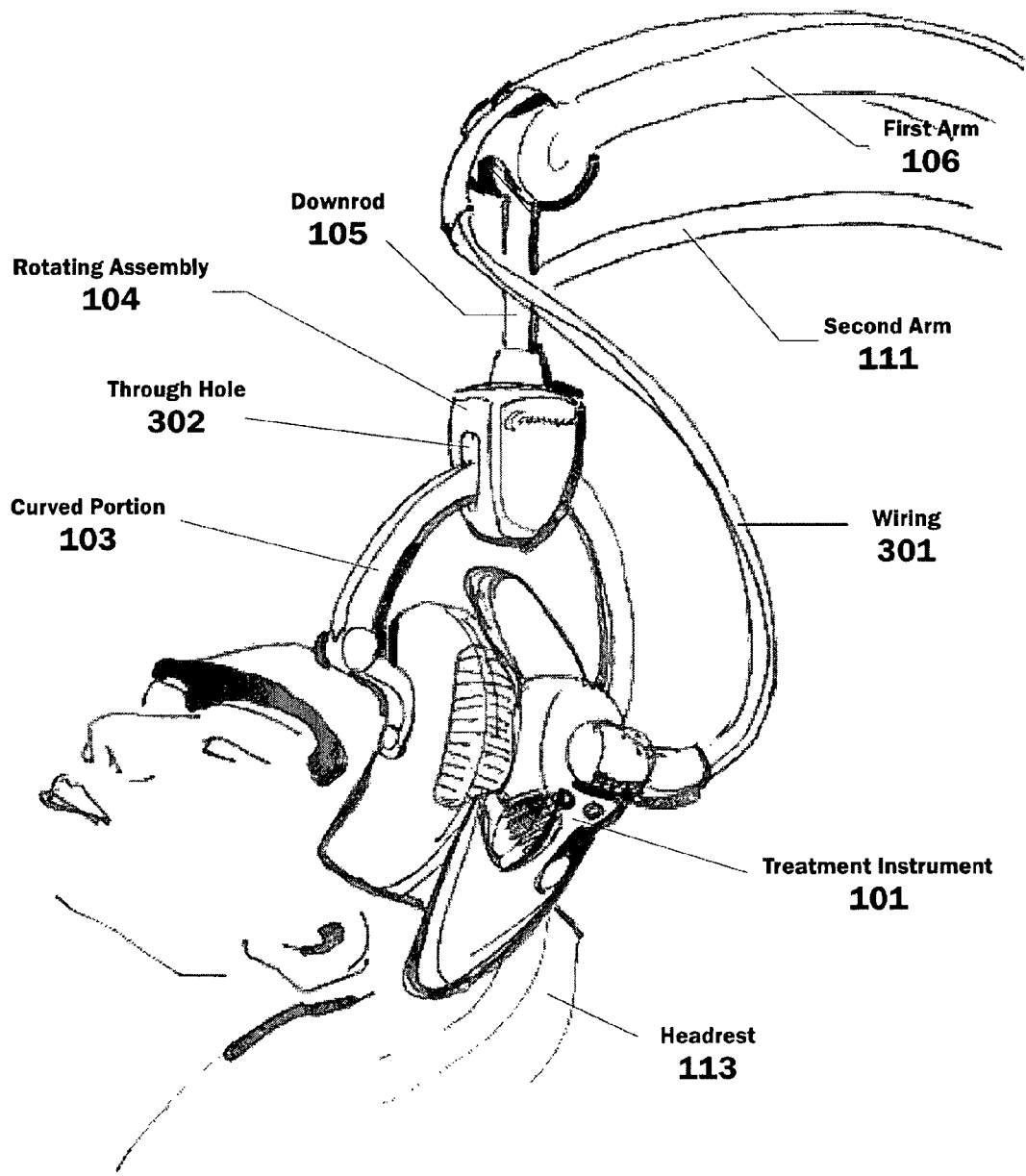
FIG. 3 illustrates a view of an example treatment instrument and holder in accordance with an embodiment of the invention.

FIG. 3 illustrates a view of an example treatment instrument and holder in accordance with an embodiment of the invention. As shown in FIG. 3 in more detail, a patient's head may be positioned on headrest 113, while a user positions treatment instrument 101. FIG. 3 also further illustrates the configuration of first arm 106, second arm 111, rotating assembly 104 and curved portion 103.

More specifically, these components are located with respect to one another and with respect to the patient to allow the device to be placed on the patient without inhibiting the patient's view. Also, FIG. 3 illustrates how the configuration of the components may permit video camera system 202 (described with reference to FIG. 2) to potentially have an unimpeded view of the patient's head as well as the components themselves. Also, wiring 301 for device 100 may be routed within or along first arm 106 to treatment instrument 101. It can be further seen in more detail the way that curved portion 103 moves through rotating assembly 104. In particular, rotating assembly 104 has a throughhole 302. Throughhole 302 may be in the shape of curved portion 103 to further facilitate movement through rotating assembly 104. For example, as shown, where curved portion 103 has an oval or rectangular profile, throughhole 302 may have an oval shape. Also, the shape of rotating assembly 104 may be such as to facilitate the particular radius of the arc for curved portion 103.

Figure 4:
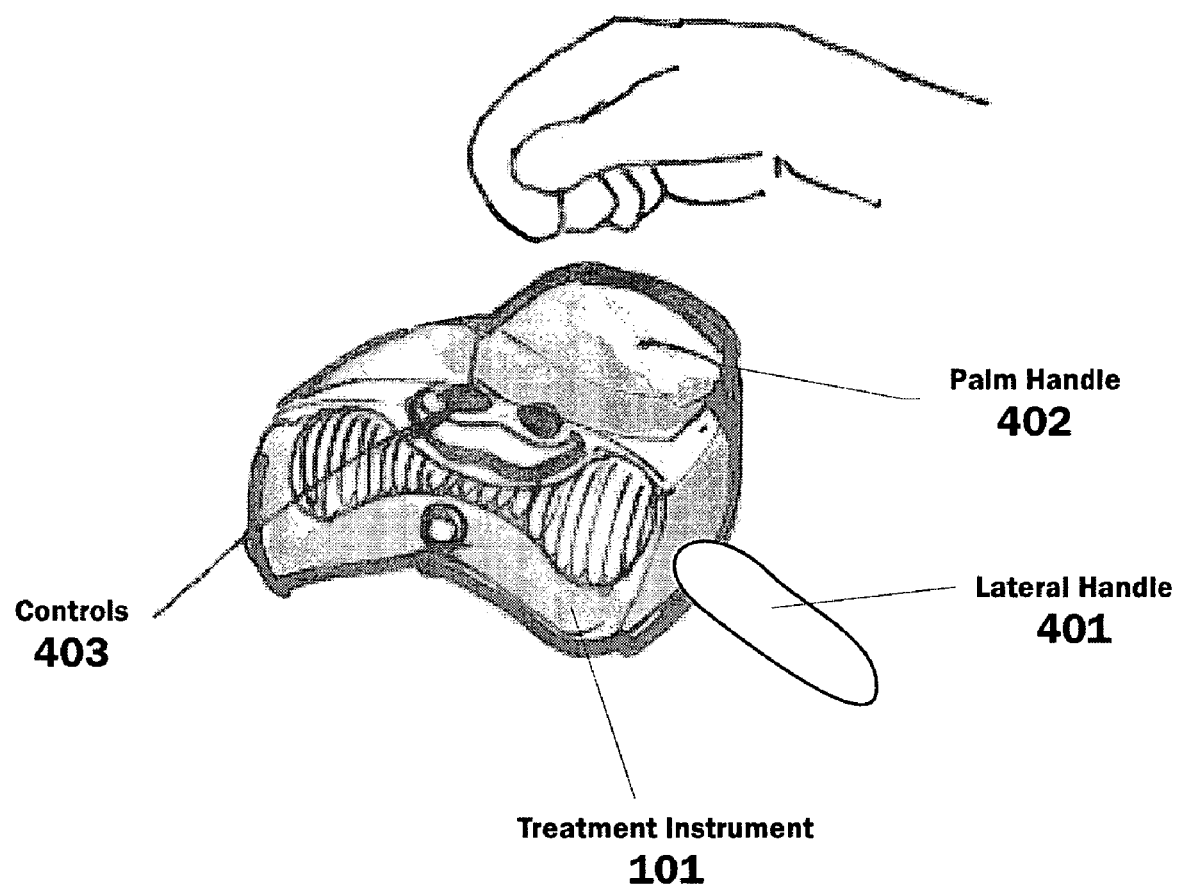
FIG. 4 illustrates a view of an example handle position for the treatment instrument in accordance with an embodiment of the invention.

FIG. 4 illustrates a view of an example handle position for the treatment instrument in accordance with an embodiment of the invention. As shown in FIG. 4, certain handles or gripping devices may be placed on treatment instrument 101 to facilitate the user's movement and positioning. For example, the user may use a lateral handle 401 and a palm handle 402 to move treatment instrument 101.

Although lateral handle 401 and a palm handle 402 are shown attached to treatment instrument 101, it should be appreciated that these and other handles may be merely in proximity to treatment instrument 101. Palm handle 402 allows the user to easily place the palm of their hand on top of treatment instrument 101. Also, lateral handle 401 allows the user to place their hand beside treatment instrument 401. The user may use both lateral handle 401 and a palm handle 402 to move and position treatment instrument 101 more easily with respect to the patient. Although two handles are shown, it should be appreciated that none, one or more handles may be included. Also, although lateral handle 401 is shown extruding from one side of treatment instrument 101, it should be appreciated that lateral handle also may extrude from more than one side and/or may be configured to move through treatment instrument 101 in a periscope-like design.

In addition to handles, treatment instrument 101 may have control buttons 403 attached thereto or located in proximity. Control buttons 403 may be used to activate and deactivate the locking mechanisms described above. Control buttons 403 may be used in either a normally off or normally on mode. For example, in normally off mode, release of control buttons 403 may activate the locking mechanism and prevent further movement of the components of device 100. This may be desirable to be consistent with locking the movement of the components when the user releases or moves their hand away from treatment instrument 101.

Also, it should be appreciated that there may be none, one or more control buttons used. In addition, instead of having dedicated control buttons, activation of the locking mechanism may occur by merely touching the handles. For example, the handles may have optic and/or pressure sensors, for example, that detect when a user has engaged treatment instrument 101 for movement.

Figure 5:
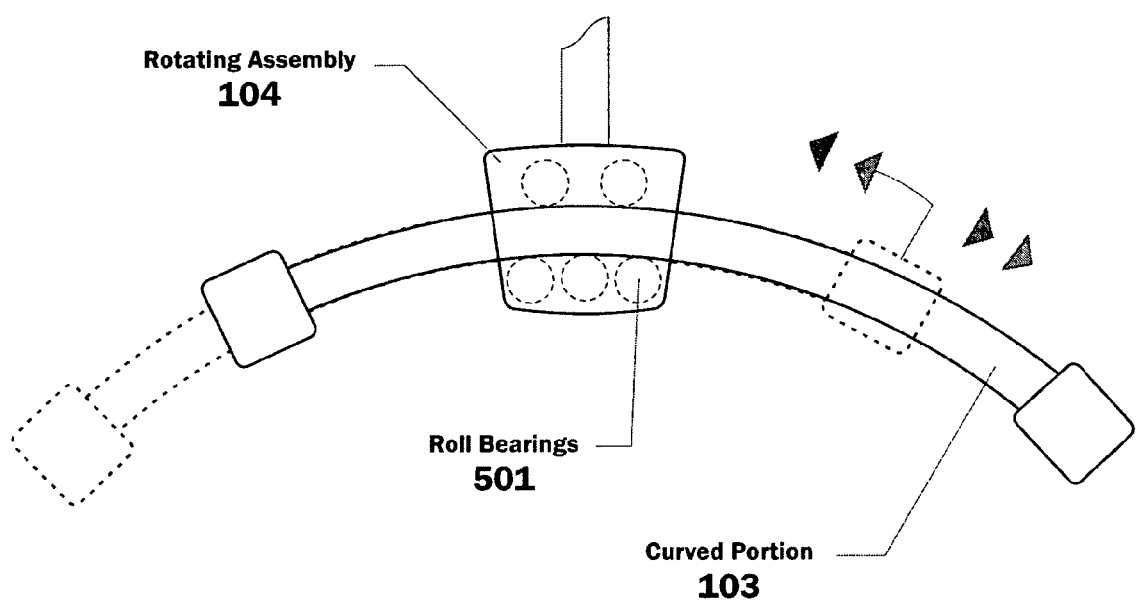
FIG. 5 illustrates an example movement component in accordance with an embodiment of the invention

FIG. 5 illustrates an example movement component in accordance with an embodiment of the invention. As shown in FIG. 5, roll or ball bearings 501 that facilitate movement among the components of device 100. For example, as shown in FIG. 5, ball bearings 501 may be used on either side of curved portion 103, so as to facilitate its movement within rotating assembly 104. Also, the number of ball bearings 501 used may depend upon the desired ease or restriction of movement between the components. In addition, although not shown, each ball bearing may include a locking mechanism (described above) or braking device that can be actuated to prevent rolling of ball bearings 501.

Although not shown headrest 113 may also include an adjustment strap that is capable of maintaining the position of the patient's head in headrest 113. Such a device may be helpful in preventing movement of the treatment instrument during treatment. The adjustment strap may include certain measurements or designated markings to facilitate subsequent use of the strap on the same patient. Also, the adjustment structure may include a malleable material that molds to the patient's head. At least a portion of the adjustment strap may span the patient's nose. Also, the adjustment strap may be reusable or may be rendered unusable following treatment of the patient.

In an exemplary embodiment, the headrest 113 is removably held in place in a fashion that facilitates quick release in the event that the patient needs to be quickly removed from the treatment apparatus as in an emergency or when the treatment must be paused. For example, a VELCRO™ patch may be provided for mating with a counterpart VELCRO™ patch on the headrest 113. Such a disconnect feature preferably allows the patient to be easily rolled onto his or her side in the remote event of seizure. Also, alignment pegs may also be provided on the headrest 113 for accepting alignment notches and/or holes in headrest 113.

In addition to a separate alignment mechanism, it should be appreciated that treatment instrument 101 itself may have molded markings or tabs in predetermined positions that allow the patient's head to align to a head registration system. Also, treatment instrument 101 could have registration features to align a strap or other securing device and provide fixed positioning of treatment instrument 101 to the patient's head during treatment. Also, any of the components of device 100 may have numeric, for example, position indicators that may be manually recorded for repeated positioning on treatment instrument 101 with respect to the patient.

Also, headrest 113 may include cushions that accept and cushion the rear of the patient's head when he/she is reclining in the chair for treatment. During use, the back of the patient's head and the patient's neck may be rested on the cushion.

The invention may be designed to position a TMS coil for treatment of central nervous system disease states using TMS therapies. While an exemplary embodiment of the invention is described with respect to the excitatory stimulation of the left prefrontal cortex for the treatment of depression, those skilled in the art will appreciate that the apparatus and techniques of the invention may be used to apply TMS therapies to many other central nervous system targets for the treatment of numerous other central nervous system diseases. For example, the positioning device of the invention may be used to position the TMS over the right prefrontal cortex of a patient for low frequency inhibitory stimulation in the treatment of depression. Those skilled in the art will further appreciate that the positioning device of the invention also may be used to position a TMS coil for the treatment of: epilepsy (above seizure locus), schizophrenia (at Wernicke's Area), Parkinson's Disease, Tourette's Syndrome, Amyotrophic Lateral Sclerosis (ALS), Multiple Sclerosis (MS), Alzheimer's Disease, Attention Deficit/Hyperactivity Disorder, obesity, bipolar disorder/mania, anxiety disorders (panic disorder with and without agoraphobia, social phobia a.k.a. Social Anxiety Disorder, Acute Stress Disorder, Generalized Anxiety Disorder), Post-traumatic Stress Disorder (one of the anxiety disorders in DSM), obsessive compulsive disorder (one of the anxiety disorders in DSM), pain (migraine, trigeminal neuralgia), chronic pain disorders (including neuropathic pain such as pain due to diabetic neuropathy, post-herpetic neuralgia, and idiopathic pain disorders such as fibromyalgia and regional myofascial pain syndromes), rehabilitation following stroke (neuro plasticity induction), tinnitus, stimulation of implanted neurons to facilitate integration, substance-related disorders (dependence and abuse and withdrawal diagnoses for alcohol, cocaine, amphetamine, caffeine, nicotine, cannabis), spinal cord injury and regeneration/rehabilitation, head injury, sleep deprivation reversal (DARPA), primary sleep disorders (primary insomnia, primary hypersomnia, circadian rhythm sleep disorder), cognitive enhancements, dementias, premenstrual dysphoric disorder (PMS), Drug delivery systems (changing the cell membrane permeability to a drug), induction of protein synthesis (induction of transcription and translation), stuttering, aphasia, dysphagia, essential tremor, Magnetic Seizure Therapy (MST), and other central nervous system disorders that may treated by the application of a magnetic field at particular locations in the brain. Of course, in each case, the treatment positions may vary; however, in each case the positioning device of the invention is useful in finding the treatment location in a repeatable manner and holding the TMS coil in the treatment position during therapy.

Those skilled in the art also will readily appreciate that many additional modifications are possible in the exemplary embodiment without materially departing from the novel teachings and advantages of the invention. For example, although the invention is described with reference to a user moving it with respect to a patient, it should be appreciated that the invention also may include a device that is moved robotically. In particular, those skilled in the art will further appreciate that the manual mechanical adjustments of the invention may be replaced by a manual or electronic articulating arm (e.g., robotic arm) with position feedback and that the coordinates may be read and manipulated using software for recordation. In other words, the software would convert real world coordinates to the coordinate system of the patient and hold the TMS coil in position during treatment.

Also, those skilled in the art will appreciate that the device may be include or alternatively have a suitable ball and socket arrangement that allows precise control of three-dimensional movements of the device.

Accordingly, any such modifications are intended to be included within the scope of this invention as defined by the following exemplary claims.

What is claimed:

1. A device for positioning a treatment instrument with respect to a patient, comprising:
   a holder for securing the treatment instrument, wherein the holder allows the treatment instrument to move about the patient;
   a first arm;
   a counterbalance;
   a vertical support coupled to the first arm at a pivot point, wherein the first arm is substantially transverse to the vertical support;
   wherein a first portion of the first arm extends in a first direction from the pivot point and a second portion of the first arm extends in a second direction from the pivot point, wherein the holder is coupled to the first portion of the first arm and the counterbalance is coupled to the second portion of the first arm;
   a second arm coupled to the vertical support and the holder such that the second arm is substantially parallel to the first portion of the first arm; and
   a vertical member directly coupled to the first arm and the second arm, wherein the vertical member is maintained in a substantially vertical orientation throughout the range of movement of the first arm.

2. The device of claim 1, wherein the counterbalance is affixed to the first arm at a position opposite the holder.

3. The device of claim 1, wherein the counterbalance holds the treatment instrument in a substantially constant position with respect to the patient.

4. The device of claim 1, wherein the treatment instrument comprises a magnetic stimulation device used for transcutaneous magnetic stimulation treatment of the patient.

5. The device of claim 4, wherein the magnetic stimulation device comprises an arc-shaped core spanning an angle of less than three hundred sixty degrees, and wherein the core comprises a highly saturable magnetic material having a magnetic saturation of at least 0.5 Tesla.

6. The device of claim 1, wherein the first arm rotates about the vertical support in a horizontal axis.

7. The device of claim 6, wherein the rotation is facilitated by a ball bearing construction.

8. The device of claim 1, wherein the first arm has a center of gravity point that is coupled to the vertical support.

9. The device of claim 8, wherein the center of gravity point allows the first arm to rotate in a horizontal axis about the vertical support.

10. The device of claim 9, wherein the rotation is facilitated by a ball bearing construction.

11. The device of claim 8, wherein the center of gravity point allows the first arm to rotate in a vertical axis about the vertical support.

12. The device of claim 1, further comprising a headrest.

13. The device of claim 12, wherein the headrest is coupled to a mobile cart.

14. The device of claim 12, wherein the headrest is coupled to the vertical support.

15. The device of claim 12, wherein the headrest is adjustable in a vertical and horizontal axis.

16. The device of claim 12, wherein the vertical support moves in horizontal plane with respect to the headrest.

17. The device of claim 1, wherein the holder has a center of gravity along one end of the first arm.

18. The device of claim 1, wherein the holder comprises a curved portion.

19. The device of claim 18, wherein the curved portion has a radius adapted to prevent the curved portion from contacting a patient's head.

20. The device of claim 1, wherein the holder comprises a rotating assembly.

21. The device of claim 20, wherein the holder comprises a curved portion that moves in an arcuate motion through the rotating assembly.

22. The device of claim 20, wherein the rotating assembly rotates 360 degrees with respect to the first arm.

23. The device of claim 22, wherein the rotation is facilitated by a ball bearing construction.

24. The device of claim 20, wherein a curved portion of the holder is locked as it moves through the rotating assembly.

25. The device of claim 1, wherein the vertical member comprises a downrod that connects a rotating assembly to the first arm.

26. The device of claim 1, wherein the vertical support moves in horizontal plane with respect to the patient.

27. The device of claim 1, wherein the vertical support is contoured to allow viewing of a display viewed between the vertical support and the holder.

28. The device of claim 1, wherein the second arm maintains the treatment instrument in a substantially constant vertical plane.

29. The device of claim 1, further comprising a locking mechanism.

30. The device of claim 29, wherein the locking mechanism prevents movement of at least one of the following: the treatment instrument, the curved portion, the rotating assembly, the vertical support, the first arm.

31. The device of claim 30, wherein the single activation movement comprises releasing a pushbutton.

32. The device of claim 30, wherein the single activation movement comprises a user releasing the treatment instrument.

33. The device of claim 29, wherein the locking mechanism is activated by a single activation movement.

34. The device of claim 29, wherein the locking mechanism is activated by a device in proximity to a location that a user grips the treatment instrument.

35. The device of claim 29, wherein the locking mechanism comprises electric relays.

36. The device of claim 35, wherein the wiring for the electric relays is concealed by at least one of the following: the treatment instrument, the curved portion, the rotating assembly, the vertical support, the first arm.

37. The device of claim 29, wherein the locking mechanism is activated by a more than one activation movement.

38. The device of claim 1, wherein the vertical support is coupled to a mobile cart.

39. The device of claim 1, wherein the vertical support rotates about a vertical axis.

40. The device of claim 39, wherein the rotation is facilitated by a ball bearing construction.

41. The device of claim 1, further comprising a first handle attached to the treatment instrument, wherein the first handle extends out from the treatment instrument along an axis defining a center of the treatment instrument.

42. The device of claim 41, wherein the first handle conforms to the shape of a hand.

43. The device of claim 1, further comprising a second handle, wherein the second handle extends above the plane of the treatment instrument.

44. The device of claim 43, wherein the second handle conforms to the shape of a hand.

45. The device of claim 1, wherein the treatment instrument comprises a non-transcranial magnetic stimulation device.

46. The device of claim 1, wherein the device is manufactured, at least in part, from metal.

47. The device of claim 1, wherein the device is manufactured, at least in part, from plastic.

48. The device of claim 1, wherein the device is adapted for use with a seated patient.

49. The device of claim 1, wherein the device permits movement of the treatment instrument with six degrees of freedom.

50. The device of claim 1, wherein the first arm does not extend beyond a plane of a mobile cart.

51. The device of claim 1, further comprising an adjustment structure that is capable of adjusting the device to each patient.

52. The device of claim 51, wherein the adjustment structure comprises a malleable material to mold to the patient's head.

53. The device of claim 51, wherein the adjustment structure prevents movement of the treatment instrument during treatment.

54. The device of claim 51, wherein at least a portion of the adjustment structure is adapted to span the patient's nose.

55. The device of claim 51, wherein the adjustment structure is reusable.

56. The device of claim 51, wherein the adjustment structure is rendered unusable following treatment of the patient.

57. The device of claim 51, wherein the adjustment structure is a head strap comprising measurement marks to indicate a position relative to a patient's head.

58. The device of claim 51, wherein the adjustment structure substantially maintains the position of the treatment instrument relative to the patient.

59. The device of claim 1, wherein the device is moved robotically.

60. The device of claim 1, further comprising a video display monitor for graphically indicating the position of the treatment instrument with respect to the patient.

61. The device of claim 1, further comprising a computing device for processing a position of the treatment instrument with respect to the patient.

62. The device of claim 1, further comprising a computing device for storing a position of the treatment instrument with respect to the patient.

63. The device of claim 62, wherein the computing device provides the stored position data for subsequent patient treatment.

64. The device of claim 62, wherein the computing device provides the stored position data to a video display monitor.

65. A system device for positioning a treatment instrument with respect to a patient, comprising:
 an articulating arm device, comprising:
  a holder for securing the treatment instrument, wherein the holder allows the treatment instrument to move about the patient, the holder comprising a vertical member;

a first arm coupled to the holder;
a counterbalance coupled to the first arm;
a vertical support attached to the first arm at a pivot point, wherein the first arm is substantially transverse to the vertical support;
wherein a first portion of the first arm extends in a first direction from the pivot point and a second portion of the first arm extends in a second direction from the pivot point, wherein the holder is coupled to the first portion of the first arm and the counterbalance is coupled to the second portion of the first arm;
a second arm coupled to the vertical support and the holder such that the second arm is substantially parallel to the first portion of the first arm, wherein the vertical member is directly coupled to the first arm and the second arm and the vertical member is maintained in a substantially vertical orientation throughout the range of movement of the first arm; and
a treatment instrument locator device, comprising:
fiducial reflectors located on the treatment instrument and the patient; and
a video camera for determining the position of the treatment instrument and the position of the patient, wherein the video camera determines the positions as a function of detecting the location of the fiducial reflectors,
wherein the video camera maintains a line of sight to at least one fiducial reflector while the articulating arm is in operation.

* * * * *